United States Patent [19]

Eberle

[11] 4,447,220
[45] May 8, 1984

[54] METHOD AND APPARATUS FOR SEPARATING BLOOD COMPONENTS

[76] Inventor: Günter Eberle, Gartenstrasse 100, 7200 Tuttlingen, Fed. Rep. of Germany

[21] Appl. No.: 186,482

[22] Filed: Sep. 22, 1980

[30] Foreign Application Priority Data

Sep. 22, 1979 [DE] Fed. Rep. of Germany ....... 2938367
Nov. 15, 1979 [DE] Fed. Rep. of Germany ....... 2946198
Apr. 1, 1980 [DE] Fed. Rep. of Germany ....... 3012708

[51] Int. Cl.³ .................. B04B 15/06; B04B 15/12
[52] U.S. Cl. ......................... 494/26; 210/927
[58] Field of Search ............. 233/26, 20, 14 R, 1 R, 233/4, 3, 13, 46, 47 R; 210/927; 128/214 R, 214 D, 194, DIG. 5; 494/26

[56] References Cited

U.S. PATENT DOCUMENTS

| | | |
|---|---|---|
| 3,674,197 | 7/1972 | Mitchell et al. ................ 233/14 R |
| 3,684,160 | 8/1972 | Unger et al. ..................... 233/20 R |
| 3,724,747 | 4/1973 | Unger et al. ..................... 233/26 X |
| 3,987,961 | 10/1976 | Sinn et al. .................... 128/214 P X |
| 4,098,456 | 7/1978 | Bayham ........................... 233/14 R |
| 4,303,193 | 12/1981 | Latham, Jr. ..................... 233/26 X |

FOREIGN PATENT DOCUMENTS

2404036  7/1975 Fed. Rep. of Germany ...... 210/927

*Primary Examiner*—Frank A. Spear, Jr.
*Attorney, Agent, or Firm*—William R. Price

[57] ABSTRACT

A cup (2) of the centrifuge has two chambers (1,3). In the first chamber is placed the first blood bag (6) filled with blood fluid, which is inserted into the chamber together with an elastically deformable inset cup (4). A pressure pad (9) bears at one end on the outside (7) of the inset cup (4) and at the other end on the inside (8) of the chamber (1) of the centrifuge. During the centrifuging, the pressure pad (9) is admitted with pressure which results in a great volume increase. The inset cup (4) is thus compressed elastically so that the blood bag (6) is compressed and the blood components centrifuged in the blood bag are transferred corresponding to the volume increase of the pressure pad (9) into an empty satellite-blood bag arranged in the adjacent chamber (2). Over the upper connecting part (81) of the blood bag projecting from the chamber (1) is pushed a holder (64) which prevents bending of the connecting tube during the centrifuging process.

3 Claims, 16 Drawing Figures

METHOD AND APPARATUS FOR SEPARATING BLOOD COMPONENTS

The subject matter of the invention is a method and an apparatus for carrying out the method for separating blood components (plasma, buffy coat, erythrocytes etc) by centrifuging the blood fluid in the rotor of a centrifuge, where the blood fluid is contained in a first blood bag in the rotor, to which is connected a second (satellite-) blood bag, whereby the separation of the components is effected by displacement of the centrifuged components from the first blood bag into one or more second blood bags.

A method of the above described type, which works with a closed system of a blood bag filled with blood fluid and an (at first) empty (satellite-) blood bag is known. Heretofore the blood bag filled with blood fluid was placed into one chamber of the rotor of the centrifuge and in the same chamber the at first empty (satellite) blood bag. Both blood bags were connected with each other over a connecting tube. Then the centrifuging was started and the erythrocytes (hereafter only called erys) settled in known manner on the bottom of the blood bag. Above the layer of erys is formed the so-called buffy coat, which forms a transition layer between the erys and the plasma deposited above the buffy coat. After the centrifuging, the first blood bag containing the centrifuged blood components had to be carefully removed from the stopped centrifuge. This blood bag was then placed in a mechanical squeezing device and compressed there slowly and carefully from the bottom to the top so that the blood plasma next to the connecting tube was squeezed out first from the blood bag. This blood plasma was conducted into the second (satellite-) blood bag by compressing the first blood bag over the connecting tube.

A disadvantage of this known method is that the erys are compressed by the squeezing, and thus arrive in a cloud in the buffy coat and in the blood plasma, so that the blood plasma is contaminated. It is thus not possible with the known method to obtain a blood plasma free of erys. Besides, the buffy coat itself was contaminated by the above described compression of the first blood bag, so that a pure buffy coat could no longer be obtained. The above-described method is also energy-and time-consuming as well as cumbersome.

The object of the present invention is to develop a method of the above-described type in such a way that separation with maximum purity of the centrifuged blood components is possible, where the separation is much simpler, faster and safer.

For the solution of this problem, the method of the above-described type is characterized in that the displacement of the centrifuged components is effected during the spinning of the centrifuge.

An essential feature of the given technical teaching is thus that it utilizes the effect that the heavy erys are kept during the spinning on the bottom of the blood bag by the centrifugal force, and that a relatively sharp separation takes place during the spinning between the erys and the buffy coat, on the one hand, and between the buffy coat and the blood plasma, on the other hand. It was found that this relatively sharp separation is only stopped after the centrifuge is stopped and after the centrifuged blood components have been displaced according to the known method of the above-described type. According to the invention, it is thus suggested to effect the separation of the centrifuged components after the centrifuged components are already available.

This has the great advantage that the sharp separating layer between the centrifuged blood components is preserved during the spinning process, and that the said blood components can be obtained relatively pure during the spinning process. This eliminates the cumbersome removal of the blood bag from the arrested centrifuge and the subsequent squeezing of the blood bag, because the separation of the centrifuged components themselves already has taken place during the spinning process of the centrifuge.

In order to facilitate the displacement, it is preferred if the displacement of the centrifuged components takes place while the rotating centrifuge cup slows down.

It was found that, due to the centrifugal force acting during the spinning process, higher pressures must be expended in the displacement than during the slowdown when the centrifugal force diminishes substantially.

For effecting the displacement during the centrifuging process, preferably during the slowdown, the following devices are described below.

In a preferred embodiment, the first blood bag filled with blood fluid is arranged together with at least one pressure pad admitted with pressure in a first chamber of the rotor, the second blood bag being arranged in a second chamber of the rotor.

According to the invention, the displacement of the centrifuged blood components from the first blood bag is effected by placing the first blood bag together with a pressure pad admitted with pressure in a first chamber of the rotor. The pressure pad is deformable and can increase its volume, depending on the pressure. Because the pressure pad is arranged together with the first blood bag in a chamber of the rotor, the first blood bag is so-to-speak reduced in its volume when the volume of the pressure pad increases. When the centrifuged blood components in the first blood bag have been deposited after the centrifuge has run for several minutes, the pressure pad increases in volume, so that the first blood bag is compressed and at least the blood component closest to the connecting tube is displaced over the connecting tube into the second blood bag arranged in the adjacent chamber. After the compression of the first blood bag and the displacement of the centrifugal blood components during the spinning process, preferably during the slowdown, the separating line between the individual centrifuged blood components is maintained without the various blood components being contaminated, e.g. by clouds of erys travelling into the blood plasma.

In a first embodiment of the present invention, the first blood bag filled with blood fluid is simply placed into the chamber of the rotor together with a pressure pad.

In a second embodiment of the present invention, the first blood bag filled with blood fluid is placed in an elastically deformable inset cup and the cup is placed into the chamber of the rotor, leaving there room for the insertion of the pressure pad. The first blood bag filled with blood fluid is thus not in direct body contact with the pressure pad, as in the first-mentioned embodiment. Rather the inset cup is provided here in between. The use of an inset cup has several advantages. First of all, the first blood bag filled with blood fluid is fixed in its upright position in the centrifuge so that the head portion of the blood bag, which is essentially not filled with blood, is also kept straight and upright during the centrifuging process. This is important to obtain pure blood components, because otherwise, when the head portion folds down, blood fluid can accumulate in the head piece itself, which does not take part in the centrifuging process and in the following displacement and separation of the centrifuged blood components, this blood fluid contaminates the blood plasma squeezed out first. It is thus provided that the height of the inset cup corresponds substantially to the length of the blood bag.

In another embodiment of the present invention, the pressure pad is already admitted with pressure before the start of the centrifuging process in order to compress the blood bag filled with blood. The blood is thus fixed in the cup inside the centrifuge, rigidly and upright, so that folding of the head piece is positively prevented.

In another embodiment of the present invention, the first blood bag filled with blood fluid is fixed in the cup of the centrifuge, suspended on its head piece. To this end corresponding suspension holes are provided in the head piece which are standardized according to DIN 58 361. Into these suspension holes are placed the hooks of a suspension device, the hooks being mounted in a guide for displacement against the force of a spring. The displacement of the guide is effected in the direction of the longitudinal axis of the blood bag, so that the force on the spring of the suspension increases the more the blood bag is pulled into the inset cup by the centrifugal force acting on it. The spring force of the suspension device prevents thus the head piece of the blood bag from folding and avoids in the same manner contamination of the centrifuged blood components.

In the above-described embodiments, the blood bags (blood bags filled with blood fluid and satellite bags) were arranged in the cup of the rotor of the centrifuge standing upright or suspended.

In another embodiment of the present invention, the blood bags are arranged horizontally in separate chambers of the rotor of the centrifuge. There are various possibilities here:

In a first arrangement, the first and second blood bags are arranged in a single horizontal plane side by side, a pressure pad being provided between two blood bags each filled with blood fluid.

In another embodiment, the blood bags filled with blood fluid are arranged in a first horizontal plane in the rotor of the centrifuge cup, while the (satellite-) blood bags are arranged in a second horizontal plane above or beneath it.

According to the above-described technical teaching, the separation of the blood components obtained by centrifuging was effected in this way that a displacement body was expanded, preferably during the slowdown of the centrifuge, which compressed the blood bag containing the blood components, so that the blood component next to the opening was first displaced from the blood bag, and additional blood components which were still in the blood bag were displaced during the further expansion of the displacement body.

The use of a separate displacement body is relatively costly, however, apart from the remote control of this displacement body, e.g. over a rotating air distributor which acts on the rotor of the centrifuge.

This is where the further development of the above-described technical teaching sets in, whose object it is to develop a method and an apparatus where the separation of the centrifuged blood components during the spinning process is faster and simpler.

The solution is effected by the displacement of plasma by the action of the centrifugal force on the centrifuged blood components contained in the first blood bag.

In contrast to the above-described technical teaching, no separate displacement body is used in the further development, rather the centrifuged blood components are displaced by centrifugal force, that is, the first component is discharged from the blood bag by the centrifugal force acting during the spinning process, which can be followed by additional components after a valve has been switched.

It is particularly preferred if the displacement of the centrifuged components takes place during the slowdown of the rotor, because it is not necessary to maintain a high circumferential speed of the rotor in order to keep the centrifuged components in the blood bag.

A preferred apparatus for carrying out the process is characterized in that one or more blood bags are arranged in a first chamber of the rotor, or the radial outward range (bottom range) of which—related to the rotor—is attached a connecting tube which is connected over a remote-controlled valve to a second blood bag.

The main feature of the apparatus is thus that a connecting tube is attached in the radially outward range of the first blood bag and is connected over a remote-controlled valve with a second blood bag.

Since the erys are the heaviest part of the centrifuged components, these erys are deposited in the radially outward part of the blood bag.

After the drive of the centrifuge has been shut off, the rotor slows down, and in this slowdown phase a remote-controlled valve is opened so that the erys flow off over the connecting tube from the first blood bag into a second blood bag.

The opening-and closing time of the valve can be controlled by an automatic control device. For example, one or more photocells can be provided on the rotor of the boiler, which determines the separating layer between the erys and the buffy coat and control the closing of the valve, depending on the displacement of the separating layer radially outward during the opening phase of the valve.

As far as it is necessary to obtain the buffy coat or the blood plasma, the erys must be discharged first in the former case, and then a three-way valve is used which is switched after the erys have been discharged so that the buffy coat flows into a third blood bag.

In order to obtain the blood plasma, it is necessary to discharge the erys and the buffy coat together into the second blood bag, after which only the blood plasma remains in the first blood bag.

In order to increase the amount of blood plasma obtained, for example, the cylindrical rotor contains sector-shaped chambers into which a first blood bag is placed. Three, four, five or more blood bags can be inserted, for example, distributed over the circumference of the rotor.

For the arrangement of the second blood bag, there are several possibilities and preferred embodiments.

In a first embodiment, the second blood bag is arranged under the first blood bag, related to the plane of rotation, and the connecting tube opens into a radially outward range of the second blood bag.

The first and second blood bag are thus arranged one under the other, which results in a particularly space-saving arrangement and a relatively small diameter of the rotor.

In a second embodiment, the second blood bags are arranged radially outward behind the first blood bags, so that the length of the connecting tube is relatively short, and the component to be separated can flow directly on the shortest route into the second blood bag. The flow is further accelerated by the action of the centrifugal force. The second blood bags can be arranged here in the same plane of rotation as the first blood bags, but they can also be arranged radially behind the first blood bags in a different plane of rotation (e.g. obliquely staggered and inclined downward).

Important in all embodiments is only that the displacement (discharge) of the respective centrifuged components takes place under the action of the centrifugal force during the spinning process (preferably during the slowdown of the centrifuge). No displacement body is required, and no control for the expansion of the displacement body. The entire arrangement can be automated if remote-controlled valves are used which are actuated without contact.

The determination of the individual separating phase between the centrifuged components can be effected automatically by means of photocells whose signals control the opening and closing phase of the remote-controlled valve over a control device.

The principle of the above-described embodiment is based on the fact that blood bags are placed outside the axis of rotation in the rotor of the centrifuge.

The two technical teachings described above suggest methods which make it possible to bring the blood plasma contained in one blood bag, after it has been centrifuged off during spinning process, into the satellite blood bag so that an extremely pure blood plasma of high quality can be obtained. The transfer of the blood plasma from the blood bag filled with fluid to the satellite blood bag is effected here by compression of this blood bag during the spinning process, so that the blood plasma next to the connecting part is displaced by compression of the blood bag into the connecting tubes, and thus into the satellite blood bag.

During the centrifuging process, bending of the connecting part of the blood bag must be avoided under all circumstances, because blood fluid is also contained in the connecting part of the blood bag, that is, in the part into which the connecting tubes and other connecting openings open. If this connecting part is bent off during the centrifuging process, which can easily happen since the blood bag is pressing during the centrifuging process with an axially directed centrifugal force against the bottom of the centrifuge cup, then blood fluid is enclosed in this part which can no longer take part in the centrifuging process.

If the plasma is to be transferred during or after the centrifuging process over the connecting part and the connecting tubes into the satellite blood bag, this plasma takes along the blood fluid contained in the previously bent connecting part so that it is contaminated. The quality and purity of the blood plasma obtained is thus greatly impaired.

In order to avoid these so-called sedimentation traps, it is known to provide spring-loaded hooks in corresponding recesses of the blood bag which keep the blood bag spring-loaded in upright position during the centrifuging process, thus preventing bending. A disadvantage of the arrangement is that the attachment and fastening of the blood bag on this hook is rather cumbersome, and that the recesses of the blood bag tend to tear out.

Furthermore it is not possible with the known solutions of the state of the art to effect a compression of the blood bag during the centrifuging process in such as way that, after the blood components in the blood bag have been obtained by centrifuging, blood plasma can be transferred during the spinning process to the adjacent satellite blood bag.

The object of the present invention is to improve an apparatus for holding blood bags of the above-mentioned type in such a way that the apparatus prevents bending or folding of the connecting part of the blood bag during the centrifuging process.

Another object of the present invention is to improve an apparatus of the above-mentioned type in such a way that compression of the blood bag is possible during the centrifuging process, which makes it possible to transfer the blood components obtained during or after the centrifuging into an adjacent blood bag while the centrifuge is rotating.

For the solution of this problem the invention is characterized according to in that the apparatus consists of a holder which is detachably connected with the connecting part of the blood bag, whose outer circumference is adapted to the inner circumference of the centrifuge cup and which can be moved in axial direction (direction of arrow) in the centrifuge cup.

An essential feature of the present invention is thus that the blood bag is held with the suggested apparatus upright safely and free of damages in the centrifuge cup. The blood bag is held here floating without the blood bag tearing out or becoming damaged. It is no longer necessary to use separate holders for each blood bag, as was the case before with the above-described spring-loaded hook.

The suggested apparatus is thus universally usable and does not depend on the size and nature of the blood bag.

The suggested technical teaching has the essential advantage that the blood bag is held upright during the centrifuging process by means of the suggested holder, and the connecting part is therefore prevented from bending; beyond that, the holder can also be moved in axial direction in the centrifuge cup.

The holder thus exerts a piston-type action on the blood bag, where the associated cylinder is formed by the centrifuge cup. The medium to be compressed is the blood bag with the blood fluid contained therein. During the centrifuging the holder acts as a piston which is pressed by the centrifugal force in axial direction against the blood bag and is thus moved in axial direction in the centrifuge cup in the direction of the bottom of the blood bag. After the separation of the blood components in the blood bag during the centrifuging is completed, a valve in the connecting tube of the blood bag can be opened by remote control during the run of centrifuge or in the slowdown phase, so that the blood component next to the connecting part of the blood bag can be discharged into an adjacent satellite blood bag over the connecting part and the connecting tubes by the compression force on the part of the holder in the blood bag.

The suggested hold thus has a double function, because it protects the connecting part of the blood bag from bending and thus avoids sedimentation traps, while it helps at the same time to obtain an extremely pure and high-quality blood plasma, so that the erythrocytes concentrated on the bottom of the blood bag are held by the centrifugal force still acting there.

In a preferred embodiment of the present invention, the holder part can be pushed over the connecting part of the blood bag. But it is also provided that the holder can be clamped or otherwise secured on the connecting part of the blood bag. If the holder is designed to be pushed over the connecting part of the blood bag, it is preferred if the holder consists of a horizontal plate in which a slot-type recess is provided, with a vertical collar with a U-shaped cross section in a top view being molded on the boundaries of the recess, which leaves a slot on one side of the plate and of the collar for the passage of the connecting part of the blood bag, with the blood bag removed from the centrifuge cup, where the connecting part passes through the slot of the plate and of the collar filling the slot-type recess.

The blood bag designed this way can then be inserted into the centrifuge cup with the plate being adapted in its outer circumference substantially to the inner circumference of the centrifuge cup, so that the holder can move easily and with play vertically in the centrifuge cup. The horizontal plate serves here as a "piston" in the "cylinder" of the centrifuge cup, while the collar extending vertically at the boundaries of the recess serves as a support for the connecting part of the blood bag. But the holder can also be connected with the blood bag by means of screws or other detachable fastening means. For example, corresponding recesses can be provided in the collar, which are aligned with associated recesses in the blood bag. A screw or any other detachable fastening means can then be put through the aligned recesses and be secured on the holder. It is also important that the collar of the holder serves as a winding reel for the connecting tubes of the blood bag. In order to prevent damage to the connecting tubes during the centrifuging process, the connecting tubes are wound around the collar of the holder and fixed on the collar. The connecting tubes can be fixed, for example, in this way that cuts are provided in the collar to hold the connecting tubes like a clamp. It must only be made sure that the connecting tubes are not bent, so that a blood component can be discharged from the blood bag over the connecting part and the adjoining connecting tubes during the rotation of the centrifuge after the blood components have been separated.

It is also essential that the force with which the blood bag is compressed by the holder depends, on the one hand, on the speed of the centrifuge, and on the other hand, on the weight of the holder. Additional weights are detachably mounted on the holder to obtain a higher or lower compression force on the blood bag with a constant speed of rotation, depending on the requirements.

The subject matter of the present invention results not only from the subject of the individual claims, but also from the combination of the individual claims with each other.

The invention will be described more fully below on the basis of the drawings, which represent several possible embodiments. Other features and advantages which are essential for the invention will result from the drawings and the description.

Figure 1:
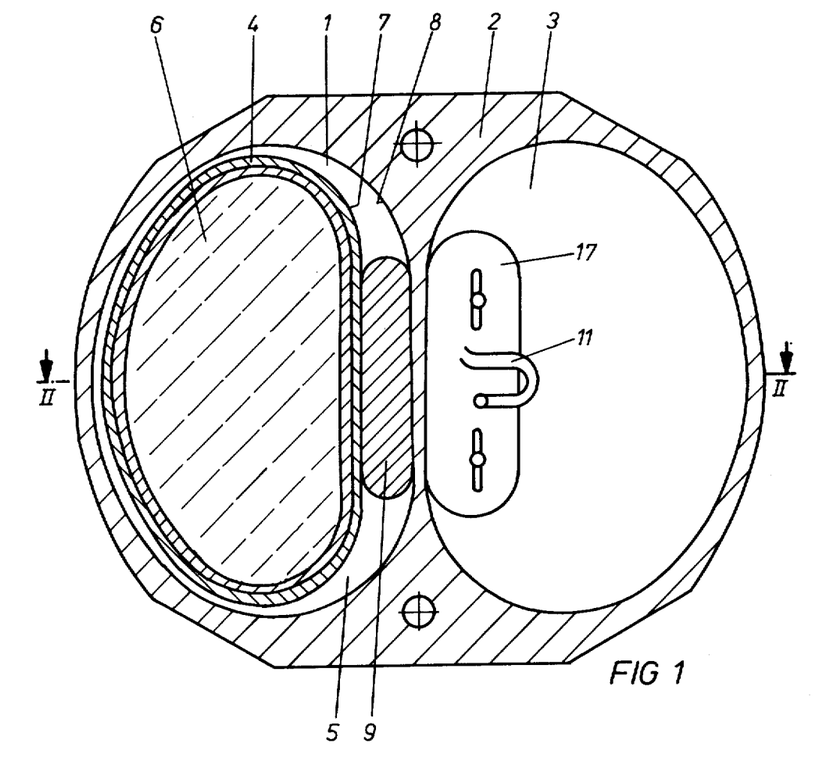
FIG. 1 shows a section through the cup of a centrifuge along line I—I in FIG. 2 in a first embodiment.
Figure 2:
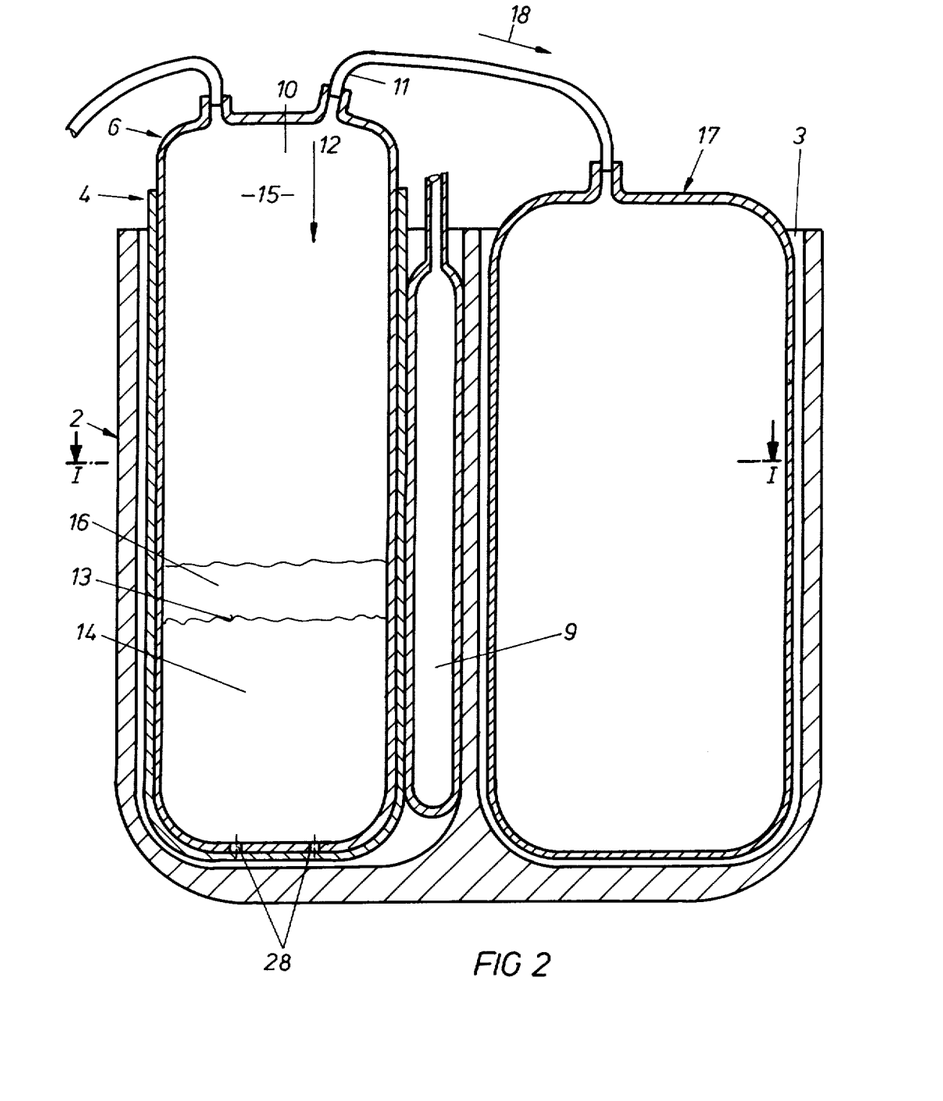
FIG. 2 shows a section along line II—II in FIG. 1

In the first embodiment according to FIGS. 1 and 2, the cup of a centrifuge is equipped with two chambers 1,3. In the first chamber 1 is placed the first blood bag 6 filled with blood fluid. Blood bag 6 surmounts with its head piece 10 the upper edge of cup 2. Blood bag 6 is inserted into an elastically deformable inset cup 4 which is so shaped according to FIG. 1 that it bears with its outside on the inner sides of chamber 1, leaving an interval 5 in the direction of the partition, where a pressure pad 9 is inserted. Pressure pad 9 bears thus, at one end, on outside 7 of inset cup 4, and at the other end, on inside 8 of centrifuge cup 2. Inset cup 4 consists of plastic material, e.g. polypropylene, or an elastically bendable metal cup etc. In order to permit the insertion of blood bag 6 in inset cup 4, the bottom of inset cup 4 is provided with bores 28 to permit the escape of air which had been displaced when blood bag 6 was inserted into inset cup 4.

On head piece 10 of blood bag 6 is attached a connecting tube 11, which is connected with the second (satellite) blood bag arranged in the adjacent chamber 3.

Before starting the centrifuging process, pressure pad 9 is admitted with pressure over its connecting tube. It is preferred if pressure pad 9 itself is filled with a fluid, e.g. a salt solution or a water-alcohol mixture. The pressure pad can thus also be used in cooling centrifuges. Compressed air is preferred for admitting the pressure fluid of the pressure pad with pressure. Compressed air is much easier to supply over correspondingly arranged rotary distributors than a corresponding pressure fluid. Besides, leaks in pumps play a much greater role in compressed air than in compressed fluid pumps.

Before the start of the centrifuging operation, pressure pad 9 is compressed so far that blood bag 6 is fixed tight and upright in inset cup 4, so that tipping of head piece 10 in the direction of arrow 12 during the centrifuging process is positively prevented.

The centrifuging process is then started. After a few minutes the various blood components have separated in the blood bag due to the centrifugal force. In the bottom part of blood bag 6 accumulate the erythrocytes (erys) 14, which are separated by a separating line 13 from buffy coat 16 above. The buffy coat itself is separated by another separating line from the blood plasma above.

During the centrifuging process—preferably during the slowdown of the centrifuge—pressure pad 9 is further admitted with pressure, which results in a great volume increase. Inset cup 4 is thus elastically compressed, so that blood bag 6 is compressed to the same degree. Due to the resulting compression, blood plasma 15 is first forced into connecting tube 11 and flows there in the direction of arrow 18 into blood bag 17 arranged in chamber 3. This way a very accurate separation between blood plasma 15 and buffy coat 16 is now possible, because the separating lines between the individual blood components remain very sharp, due to the centrifugal force which is still active, and contamination of the blood plasma by the erys is prevented in each case.

In a further development of the embodiment according to FIGS. 1 and 2 (not shown in the drawings), not only one second blood bag 17 is provided in chamber 3, but a second or third blood bag 17. These blood bags 17 would all be connected by the connecting tube, and a two-way valve would be provided in the respective connecting tube. Here the blood plasma 15 is first introduced into the first blood bag 17 by admitting pressure pad 9 and compressing blood bag 6. Then the two-way valve is switched and buffy coat 16 adjoining blood plasma 15 is introduced into the second blood bag 17. Only the separated erys remain then in blood bag 6.

Due to the use of an inset cup 4, blood bag 6 is extremely easy to handle. We can also proceed according to the above described method in this way that blood bag 6 is removed together with the inset cup after the centrifuging and inset cup 4 itself is squeezed out. The inset cup is then inserted together with blood bag 6 placed therein into a conventional squeezing device. It is preferred if inset cup 4 has a flat bottom, so that it can be placed directly on the bottom. The inset cup can then be compressed with the hand in its elastic upper range so that erys and blood plasma can now be separated too in a very simple manner without the use of a mechanical device.

Due to the fact that inset cup 4 is open at the top and has a flat bottom, the inset cup can practically only be compressed at the top. This has the advantage that the erys are not compressed at the bottom and thus do not penetrate into buffy coat 16 and blood plasma 15, so that here too a relatively clean separation of the centrifuged blood components is achieved.

In a further development of this embodiment, the elasticity of insert cup 4 is adjustable. To this end are provided fins or recesses, so that the compressibility of inset cup 4 can be varied, depending on the case, for example, only in the upper range, or in the upper range halfway down the inset cup etc.

Figure 3:
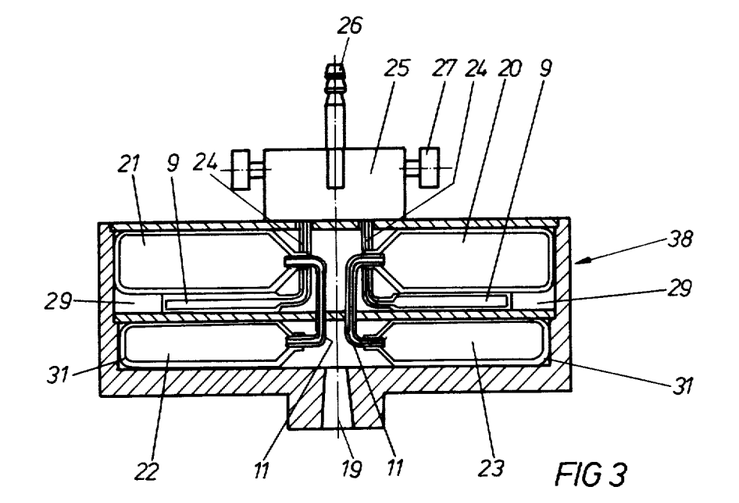
FIG. 3 shows a section through the rotor of a centrifuge in a second embodiment
Figure 4:
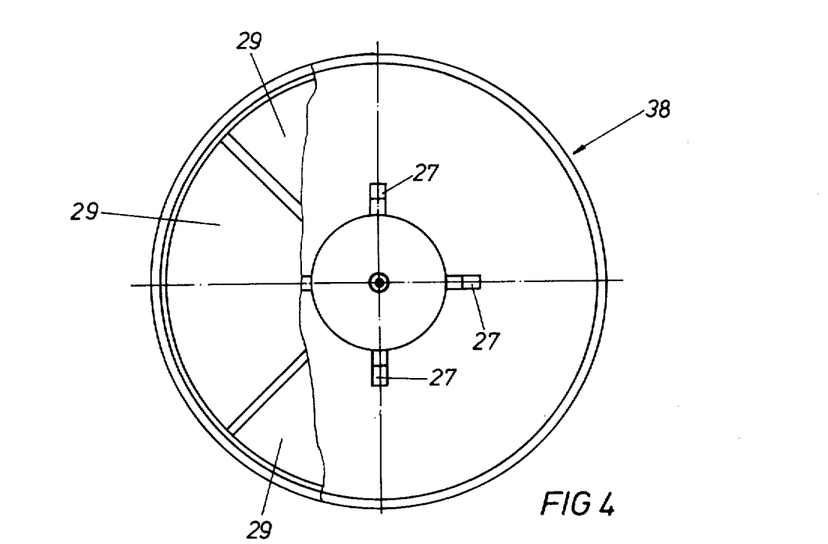
FIG. 4 shows a top view of the rotor according to FIG. 3 with the cover partly broken off

FIGS. 3 and 4 show another embodiment of the present invention, where horizontal chambers 29, 31 are superposed in a rotor 38 of a centrifuge. The chambers are divided into sectors according to FIG. 4, and a correspondingly shaped blood bag 20,21 (filled with blood fluid) and a (satellite-) blood bag, 22, 23 are arranged in each chamber 29, 31.

In order to avoid an imbalance of rotor 38, the associated blood bags 21, 22 and 20, 23 esp. must be arranged symmetrically with regard to axis of rotation 19.

Corresponding to the foregoing description, the blood-filled bags 20, 21 are connected over connecting tubes 11 with the (satellite-) blood bags 22,23.

Below each blood bag 20,21 filled with blood fluid is arranged a pressure pad 9 which is connected over connecting tubes 24 to a rotary compressed-air distributor arranged in axis of rotation 19. 27 indicates the various connections and valves. The compressed air for admitting the pressure pad 9 with pressure is supplied to rotary distributor 25 through connection 26.

According to FIG. 3, connecting tubes 11 are so arranged that blood plasma 15, as the lightest component of the blood fluid, is displaced first from blood bag 20, 21 during the expansion of pressure pad 9. But connecting tubes 11 can also be arranged in the bottom region of blood bags 20,21 (hence on the radially outward part of blood bags 20,21), so that erythrocytes 14 are first displaced into (satellite-) blood bags 22,23 during the expansion of pressure pad 9.

It is also possible to distribute the various separated blood components over different empty blood bags 22,23 by corresponding switching valves.

Figure 5:
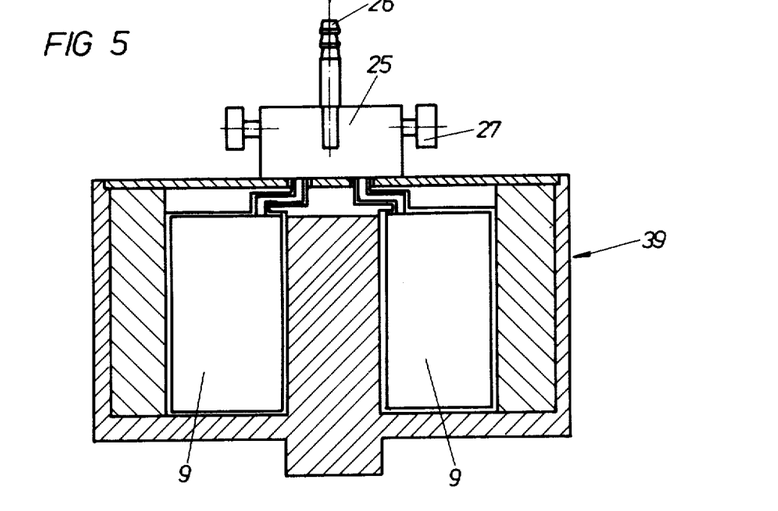
FIG. 5 shows a section through the rotor of a centrifuge in a third embodiment
Figure 6:
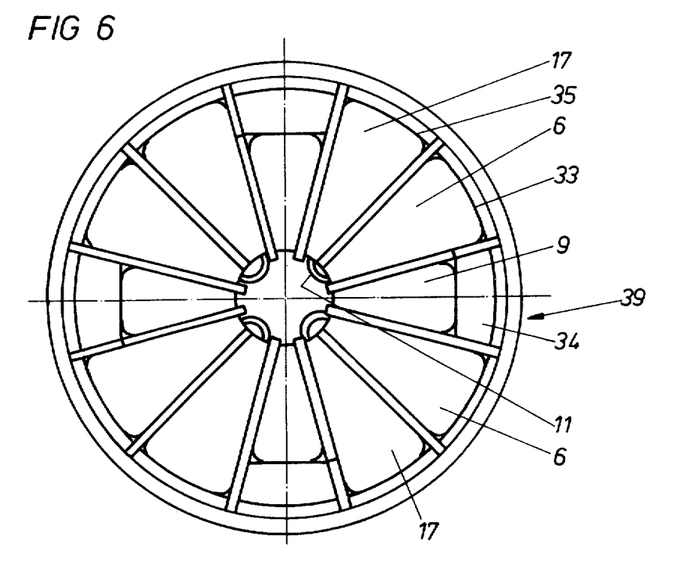
FIG. 6 shows a top view of the rotor according to FIG. 6 with the cover removed

The embodiment according to FIGS. 5 and 6 differs from the embodiment in FIGS. 3 and 4 in that blood bags 6 are arranged with (satellite-) bags 17 on one plane of the rotor 39. The said blood bags 6,17 are arranged upright according to FIG. 3 and are again connected over connecting tubes with a rotary distributor 25. Blood bags 6,17 are arranged here in separate chambers 33,35 of rotor 39 of the centrifuge. Between blood bags 6 filled with blood fluid is arranged a pressure pad 9 which bears radially outward on a support 34. During the expansion of pressure pad 9, two blood bags 6 are thus compressed at the same time, which has advantages in terms of a smaller number of connecting tubes and connections on rotary distributor 25. The connection between blood bags 6 and 17 can be established according to FIG. 6 both on the radially inward end of the blood bags and on the radially outward bottom region of blood bags 6,17.

Figure 7:
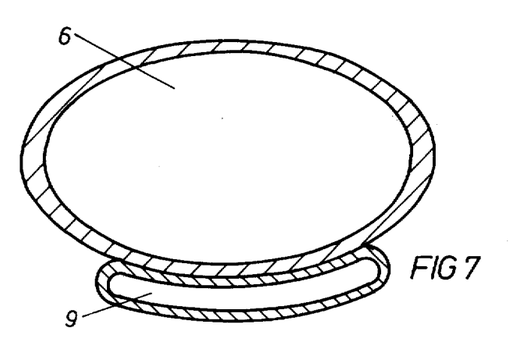
FIG. 7 shows another embodiment where the pressure pad is integral with the blood bag and made of the same material

FIG. 7 shows a different embodiment of a blood bag 6, compared to FIGS. 1 and 2. Here blood bag 6 and pressure pad 9 cannot only be separate, they can also be integral and even consist of the same material. In the represented case, pressure pad 9 can be welded or cemented on blood bag 6 or the double wall between pressure pad 9 and blood bag 6 shown in the drawing can be omitted and replaced by a single wall. Such a blood bag 6 can then be sold as a unit together with the attached pressure pad.

The second variant of the method will be described on the basis of FIG. 8.

Figure 8:
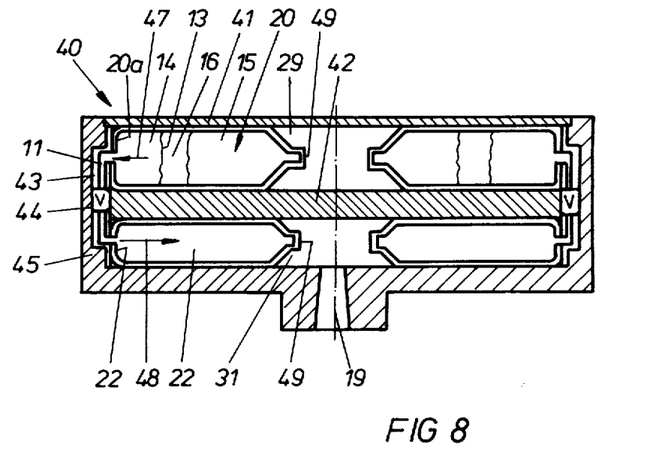
FIG. 8 shows schematically the center cross section through the rotor of a centrifuge in a first embodiment

The tank-type rotor 40 of the centrifuge according to FIG. 8 contains an insertable intermediate plate and a cover plate 41 covering the top side of the rotor tank.

Figure 9:
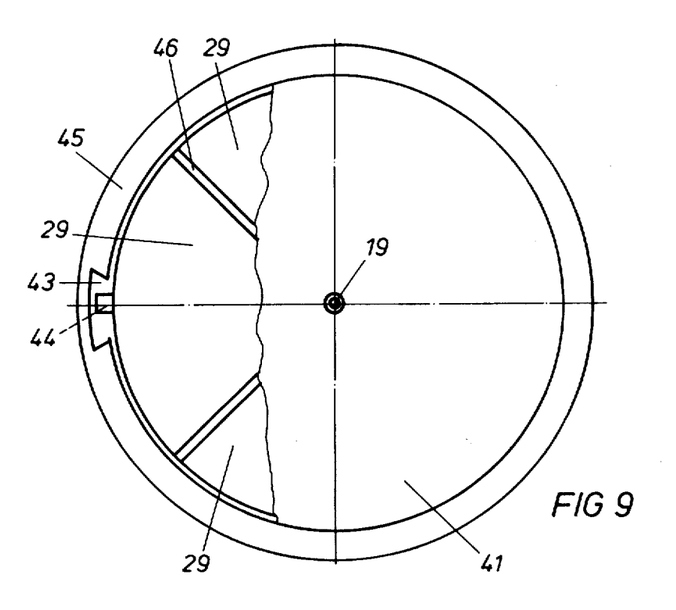
FIG. 9 shows a top view of FIG. 8 with the cover plate partly broken off

Due to cover plate 41 and intermediate plate 42, two separate chambers 29 and 31 are formed. Chambers 29,31 are subdivided by radial partitions 46 into sectors on the circumference according to FIG. 9.

The blood fluid is filled into the first blood bag 20, while the second blood bag 22 in chamber 31 is at first empty. On the bottom region 20a of blood bag 20 is attached a connecting tube 11 which opens over a valve 44 into the bottom region 22a of blood bag 22.

After the centrifuging process is completed, the components of the blood fluid separated by centrifuging are contained in separate layers in the first blood bag 20.

The erys are deposited on the radially outward part separated by a separating layer 13 from buffy coat 16, which in turn is separated by a separating layer from the radially inward blood plasma 15.

In order to obtain the blood plasma, valve 44 is opened by remote control during the centrifuging process, preferably during the slowdown of the centrifuge, so that the erys 14 leave blood bag 20 in the direction of arrow 47 to arrive through connecting tube 11 in the second blood bag 22 in the direction of arrow 48.

Furthermore the buffy coat is discharged so long until only blood plasma 15 is in the first blood bag 20. Valve 44 is then closed, so that blood plasma 15 is obtained in extremely pure form in blood bag 20.

In order to permit an outlet of the components to be separated to the first blood bag 20 and filling into the second blood bag 22, corresponding to vent holes 49 are provided.

To make sure that connecting tube 11 and valve 44 are not damaged during the centrifuging operation on jacket 45 of the rotor 40, jacket 45 is provided in this range with a recess 43 in which valve 44 and connecting tube 11 are arranged.

Instead of using a two-way valve (valve 44), it is also possible to use a multiway valve and a corresponding number of blood bags 22, if not only one blood component is to be obtained (e.g. blood plasma 15), but several components, such as blood plasma 15 and buffy coat 16.

In this embodiment it is also important that blood bags 20 and 22 are arranged outside axis of rotation 19.

The device for holding the blood bags will now be described with reference to FIGS. 10 to 16.

Figure 10:
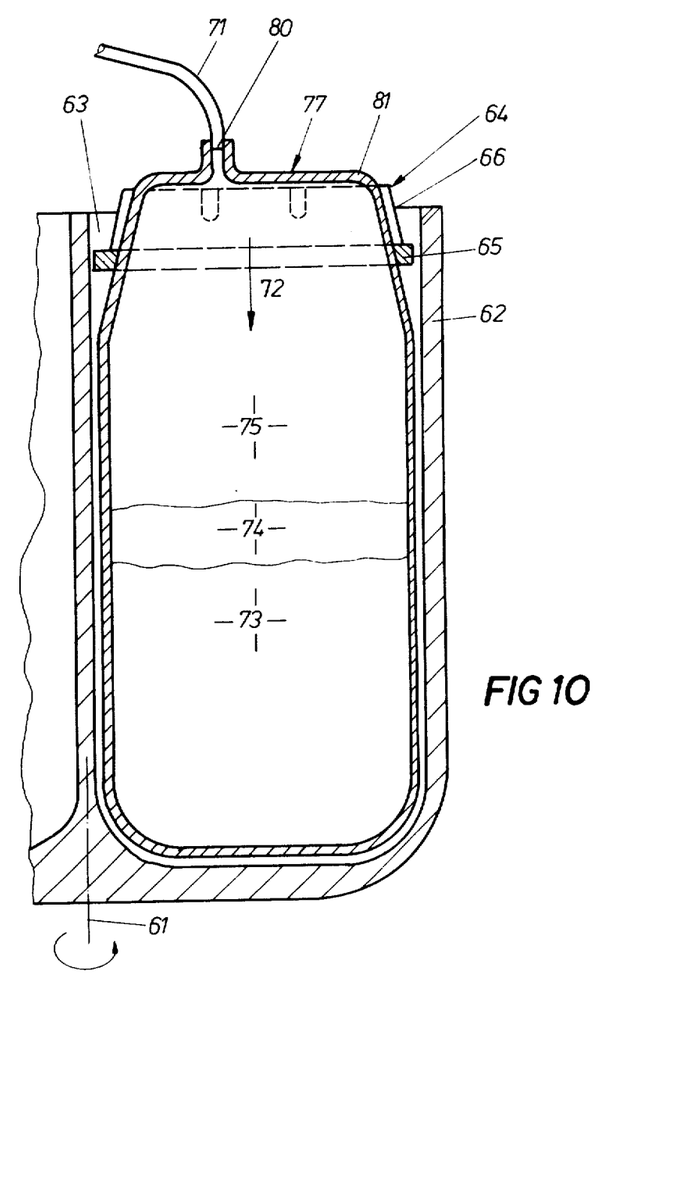
FIG. 10 shows schematically a longitudinal center cross section through half a centrifuge cup with blood bag and attached holder

FIG. 10 shows the right half of a centrifuge cup, which is exactly mirror-inverted symmetrically to axis of rotation 19. The satellite blood bag is then arranged, for example, in the left part of the centrifuge cup, not shown here.

Into central recess 63 of centrifuge cup 62, shown on the right, is inserted a blood bag 77. The blood bag consists in known manner of plastic material which is composed of two film sheets which are welded together at their circumferential edges. On the top side of the blood bag is arranged a connecting part 81, where one or more connecting tubes 71 open over one or more connecting pieces 80 into blood bag 77. In addition, closable individual openings (not shown) or other modifications can be provided on connecting part 81.

Figure 11:
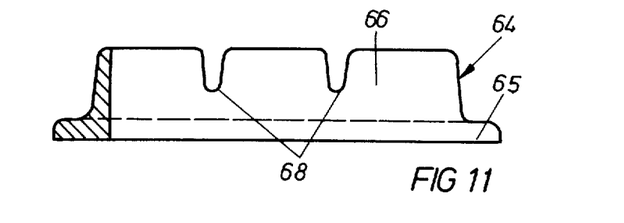
FIG. 11 shows a side elevation with a partial section through the holder
Figure 12:
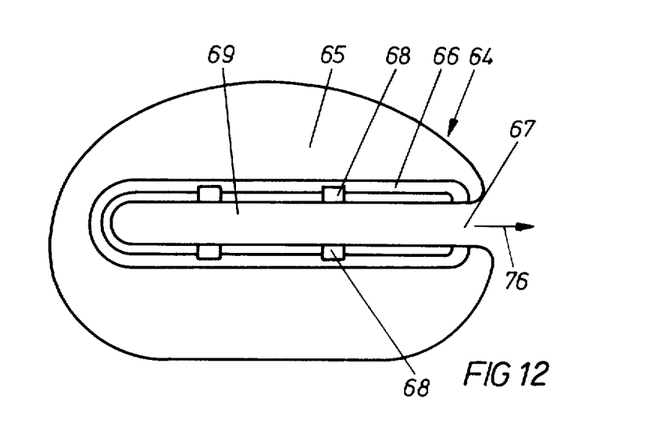
FIG. 12 shows a top view of the holder according to FIG. 11
Figure 13:
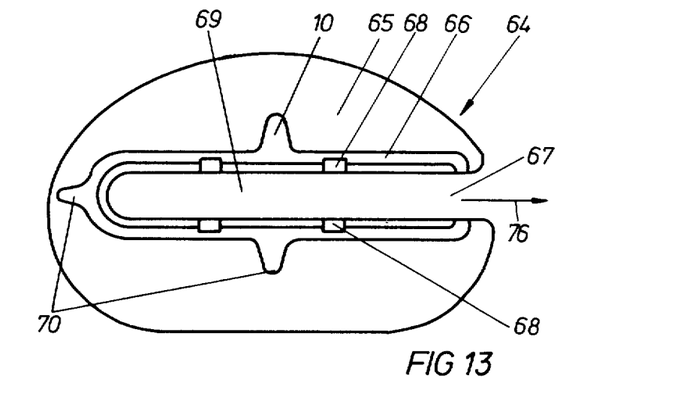
FIG. 13 shows a design of the holder similar to FIGS. 11 and 12 in another embodiment.

Over connecting part 81 of the blood bag is pushed according to FIG. 10 a holder 64 which consists of a substantially horizontal plate 65 in which is provided according to FIGS. 11-13 a slot-type recess 69 on the boundaries of which is molded a circumferential vertical collar 66, which is U-shaped in a top view, which leaves on one side of plate 65 and of collar 66 a slot 67 for the passage of connecting part 81 of blood bag 77.

During the centrifuging, a strong centrifugal force acts in the direction of arrow 72 on the blood bag and holder 64. Both parts are thus pressed against the bottom of centrifuge cup 62, whereby connecting part 81 of blood bag 77 is protected against bending in the direction of arrow 72 because it is guided on both sides by the circumferential vertical collar 66 of holder 64. Holder 64 and connecting part 81 of the blood bag thus perform during the centrifuging process an axial movement in the direction of the bottom of centrifuge cup 62, so that blood bag 77 is compressed.

After the centrifuge has run for a certain time, the blood components to be obtained by centrifuging are now separated in blood bag 77. Next to the bottom of blood bag 77 is a layer of erythrocytes, which pass over into blood plasma 75 over a boundary layer (buffy coat 74).

During the centrifuging, blood plasma 75 can now be discharged over connecting part 81 and connecting tube 71, because holder 64 compresses blood bag 77 in the direction of arrow 72 by centrifugal force still acting there and the resulting pressure increase discharges blood plasma 75 over connecting tube 71 if the valve in connecting tube 71 is opened during the centrifuging process. A blood plasma 75 of extremely high purity is thus obtained, since the erythrocytes 73 and the buffy coat 74 are kept on the bottom of blood bag 77 by the centrifugal force and accidental mixing of buffy coat 74 and erythrocytes 73 with blood plasma 75 is thus avoided.

FIGS. 11 and 12 show that collar 66 can serve at the same time as a winding reel for connecting tube(s) 71. Connecting tube 71 is wound several times around collar 66 and is then parallel to the surface of plate 65. To make sure that connecting tube 71 is not detached accidentally from collar 66, lateral cuts 68 are provided in collar 66 in which connecting tube 71 can be clamped. The entire holder 64 is pushed laterally in the direction of arrow 76 with slot 67 and the adjoining recess 69 over connecting part 81 of blood bag 77 until holder 64 has reached the position shown in FIG. 10.

In order to improve the winding of connecting tubes 71 on collar 66 lateral extensions 70 can be provided on the upper boundary of collar 66 according to FIG. 13 which extend in their plane parallel to plate 65 and which are spaced from plate 65. This yields a winding space for connecting tube(s) 71.

Figure 14:
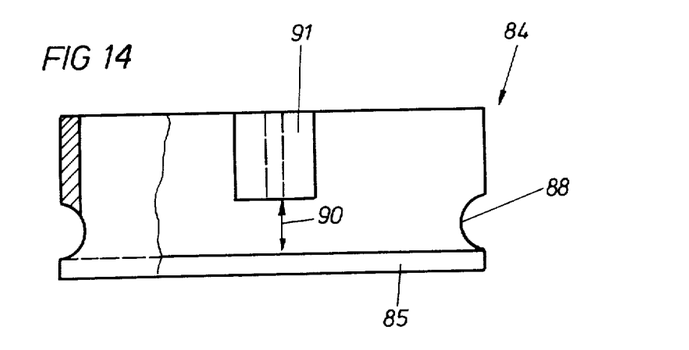
FIG. 14 shows a side elevation of the holder in a second embodiment
Figure 15:
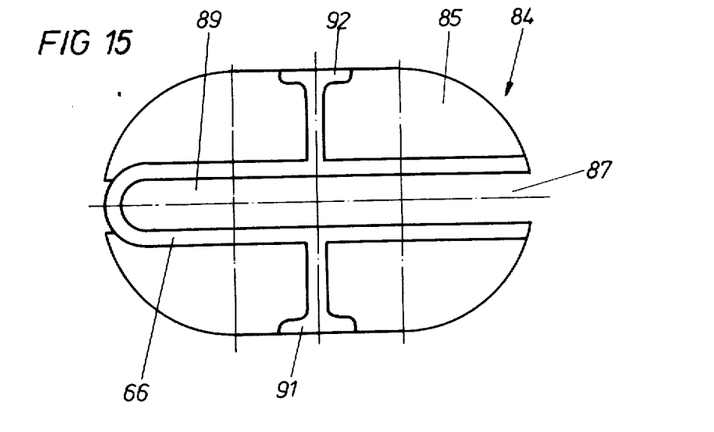
FIG. 15 shows a top view of the holder according to FIG. 14

FIGS. 14 and 15 show the embodiment of a second holder 84 which differs in essential details from holder 64 described above. Holder 84 consists likewise of a horizontal oval plate 85 with a vertically rising collar 86. Laterally on the upper edge of collar 66 are provided extensions 91, 92, which are T-shaped in a top view, the leg of the T-section starting on collar 66 of holder 84. The widened faces of extensions 91, 92 thus point to the outside of and are aligned subtially with the outer boundaries of plate 85. Holder 84 thus bears with the faces of extensions 91, 92 both on the insides of the inset cup 94 shown in FIG. 16, and also on additional parallel holders 84 arranged opposite each other.

Figure 16:
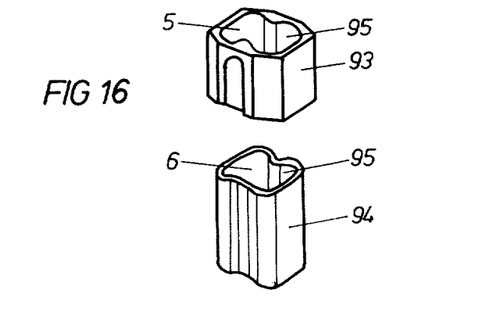
FIG. 16 shows a perspective view of a slotted suspension and of a cup to receive two blood bags and two holders.

According to FIG. 16, inset cup 94 has two openings 95, 96 which each receive blood bags. In each opening 95, 96 is inserted a holder according to FIGS. 14 and 15. The passage from one opening 95 to the other opening 96 is open.

Here bear the surfaces of extensions 91 and 92 of the juxtaposed holders 84, which face each other and support each other.

Inset cup 94 is then engaged in slotted suspension 93, and slotted suspension 93 is inserted into the head of the centrifuge.

Essential in this embodiment is thus that several holders 84 are used in an inset cup 94, and that the holders 84 support each other.

It is essential that a space 90 is formed according to FIGS. 14 and 15 between the top side of plate 85 and the bottom edge of extensions 91, 92 to receive the connecting tubes of the blood bags. The connecting tubes are thus wound into the circumferential radial slot 88 of holder 84.

In order to secure the blood bag on the holder, holder 84 is pushed according to the foregoing description with slot 87 over the blood bag. The upper part of the blood bag then extends through recess 89 of collar 66.

I claim:

1. A centrifuge for the separation of blood components which comprises:
   A. a rotor;
   B. a plurality of expandable blood bags disposed in said rotor for rotation therewith, said blood bags comprising:
      1. a first series of blood bags, each bag of said series being adapted for holding an amount of whole blood,
      2. a second series of blood bags, equal in number to the number of blood bags of said first series, each bag of said series being adapted to receive a separated blood component from one of the bags of said first series;
   C. a plurality of connecting tubes, equal in number to the number of bags of said first series, one of each of said tubes being connected to one bag of each said first and second series, so as to define a flow path between each bag of said first series and a corresponding bag of said second series;
   D. fluid pressure responsive displacement bodies, said bodies being adapted to be placed between blood bags of said first series;
   E. fluid pressure means for expanding said fluid pressure responsive displacement body during operation of the centrifuge, and thus simultaneously squeeze a controlled amount of liquid from the two blood bags;
   F. a series of partitions projecting radially from the axis of rotation of said rotor, and defining a series of expandable pie-shaped chambers;
   G. a support member, in the form of a modified trapezoid (34, FIG. 6), for insertion between two of said radiating partitions and in direct contact with the said fluid pressure responsive displacement body so that expansion of said displacement body applies radial pressure against said support member and against two of the blood bags of the first series disposed in adjacent pie-shaped chambers.

2. In combination with a centrifuge cup, an insertable device for holding a blood bag within said cup vertically, so as to prevent the bending of the connecting part (81) during the centrifuging process, said device comprising a holder (64, 84) made of rigid non-deformable material and arranged to be slipped onto the connecting part (81) of the blood bag (77) and having an opening (67,87) for receiving the connecting part (81) and having an outer circumference adapted to fit in mating engagement with the inner circumference of said inset cup, in which the holder includes:
   A. an oval plate (65,85) having a slot-type recess, which defines boundaries when viewed from the top forming a U-shaped vertical collar (66), said plate on one side (65, 85) forming a slot with said collar (66) for receiving the connecting part (81) of the blood bag (77).

3. A device, as defined in claim 2, in which the upper circumferential edge of the collar contains lateral extensions (70,91,92) formed on the plate (65, 85) and which are disposed substantially parallel to it.

* * * * *